(12) United States Patent
Rubin et al.

(10) Patent No.: US 6,438,256 B1
(45) Date of Patent: Aug. 20, 2002

(54) METHOD OF QUANTIFYING VISUAL UNIFORMITY OF PLANAR OBJECTS

(75) Inventors: Barry Rubin, Glen Mills, PA (US); Michael James Merrill, New Castle; Robert Vincent Canning, Jr., Bear, both of DE (US); Thomas William Simpson, III, Boothwyn, PA (US); Mark E. Lewittes, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/297,700

(22) PCT Filed: Nov. 6, 1997

(86) PCT No.: PCT/US97/19931

§ 371 (c)(1), (2), (4) Date: May 5, 1999

(87) PCT Pub. No.: WO98/20326

PCT Pub. Date: May 14, 1998

Related U.S. Application Data

(60) Provisional application No. 60/029,888, filed on Nov. 8, 1996.

(51) Int. Cl.[7] .................................................. G06K 9/00
(52) U.S. Cl. ...................................... 382/108; 358/448
(58) Field of Search ................................. 382/108, 312, 382/140, 141, 274, 299, 222; 358/448, 461

(56) References Cited

U.S. PATENT DOCUMENTS

| | | | | |
|---|---|---|---|---|
| 3,859,537 A | * | 1/1975 | Wolf | 250/559 |
| 4,656,663 A | | 4/1987 | Jansson et al. | 382/8 |
| 4,931,657 A | | 6/1990 | Houston et al. | 250/559 |
| 5,146,351 A | | 9/1992 | Maehara | 358/448 |
| 5,343,308 A | | 8/1994 | Johnston | 358/445 |
| 5,533,139 A | * | 7/1996 | Parker et al. | 382/108 |
| 5,909,244 A | * | 6/1999 | Waxman et al. | 348/222 |

FOREIGN PATENT DOCUMENTS

| | | | | |
|---|---|---|---|---|
| EP | 0164222 | 5/1985 | | H04N/1/38 |

* cited by examiner

*Primary Examiner*—Andrew W. Johns
*Assistant Examiner*—Seyed Azarian

(57) ABSTRACT

An improved image analysis method to quantify uniformity of visual appearance of planar objects. The measurements are substantially independent of both the image shading and the overall lightness differences among the objects.

10 Claims, 10 Drawing Sheets

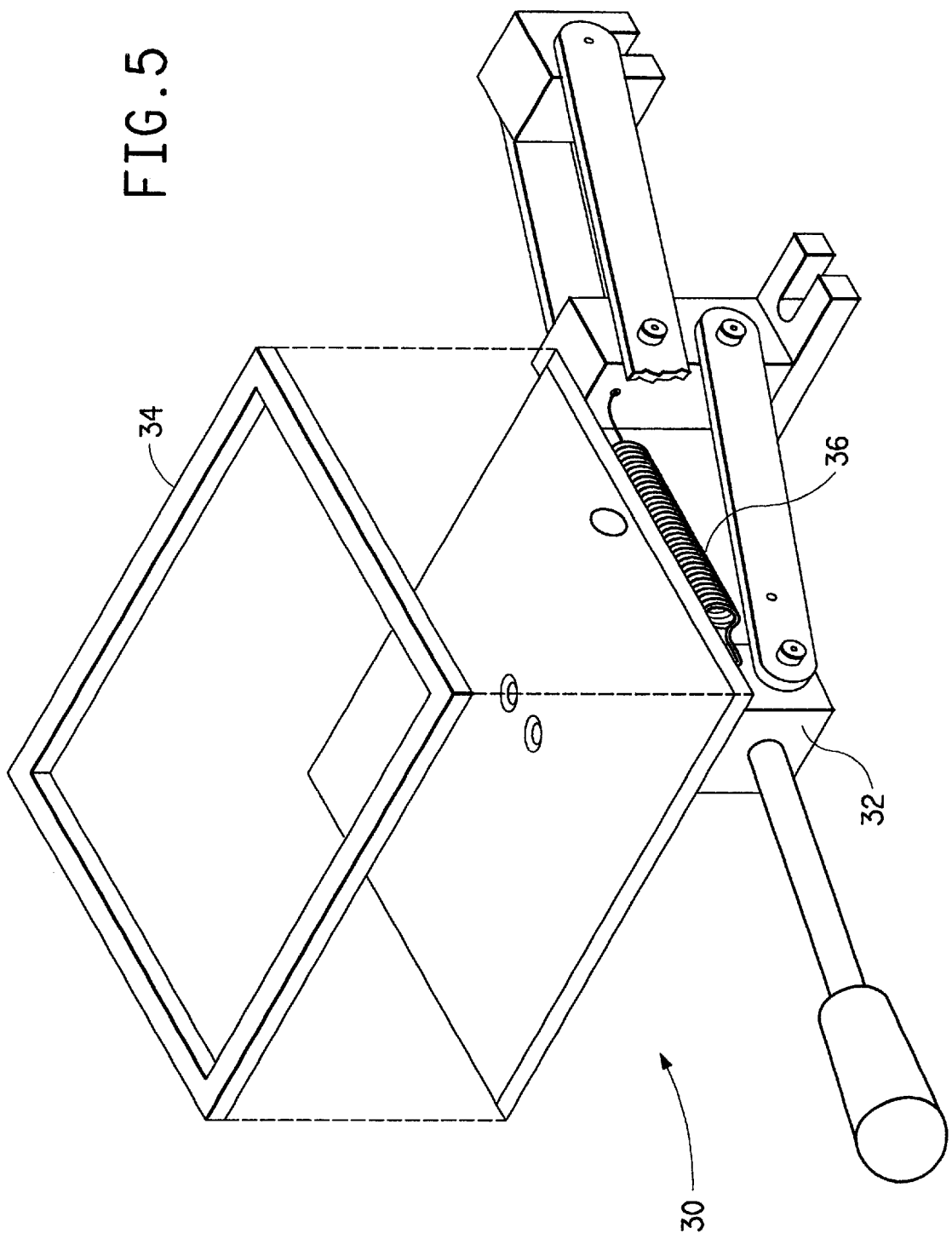

METHOD OF QUANTIFYING VISUAL UNIFORMITY OF PLANAR OBJECTS

Provisional Appl. No. 60/029,888 filed Nov. 8, 1996.

BACKGROUND OF THE INVENTION

The uniformity of surface appearance is a key attribute of many planar products, particularly coated paper products, such as paperboard. Coatings containing optical opacifiers, such as $TiO_2$, provide hiding power and visual appearance uniformity in these products. A highly uniform appearance is desired in these products. The visual uniformity is related to both surface smoothness and coating thickness uniformity. Although the surface of a coating itself may be level, an objectionable mottled appearance may be caused by thickness variations of the coating which are typically caused by unevenness of the underlying surface that passed through the coating apparatus.

There is no objective definition of mottle. Mottle is usually evaluated by trained human operators who make subjective ratings of the surface appearance based on visual observations of the coated surface. Visual ratings by a number of human observers are typically employed to establish a uniformity scale which serves as an evaluation criterion. Performance of an automated imaging system, such as that of the present invention, may be evaluated against such a criterion.

For most coated surfaces, particularly coated paperboard surfaces, the reflectance variation to be quantified is quite small. The actual reflectance variation of a coated paperboard surface is typically less than the variation in apparent reflectance (shading) caused by nonuniformity of illumination of the surface and is sometimes even less than the nonuniformity of camera response across an image of the surface.

Since the uniformity of a typical reflectance reference standard is comparable to the uniformity of some of the paperboard samples to be evaluated, prior art background correction techniques used in image processing, such as that of U.S. Pat. No. 4,656,663, are usually inadequate. Overall lightness (average reflectance) differences that exist between the paperboard samples necessitates that the measurement of visual uniformity be independent of overall lightness. Because of these factors, the prior art methods do not produce accurate, reproducible results.

SUMMARY OF THE INVENTION

The present invention is an improved image analysis method to quantify visual appearance uniformity of the surface of substantially planar objects. The measurements resulting from the method of the present invention, which are substantially independent of both the image shading and the overall lightness differences among the objects, can be correlated with the human visual ratings to an $R^2$ correlation factor greater than 0.90. The improved image analysis method comprises: (a) utilizing an analog to digital converter whose dynamic range may be set to a first, full, range and set to a second, contrast enhanced, range; (b) establishing transformation factors based upon the lower and upper limits of the first range and the second range of the analog to digital converter; (c) creating a frame-averaged modified dark current image representing the response of the photodetector array in the absence of light; (d) setting the analog to digital converter to map the contrast enhanced camera voltage range to the full grey level output range; (e) illumination the surface to the object with the light source, the output of the light source being set to an initial output level; (f) creating a frame-averaged image of the surface of the object; (g) determining the average grey level in the image; (h) adjusting the illumination level of the object by adjusting the output of the light source and repeating steps (f) and (g) until the average light level reflected by the surface of the object causes an average grey level in the image of step (g) to be within a predetermined range of the midpoint of the enhanced contrast dynamic range of the analog to digital converter; (i) creating a frame-averaged image of the surface of the object; (j) creating a dark-current corrected image by subtracting the frame-averaged modified dark current image of step (c) from the frame-averaged image of the surface of step (i) on a pixel by pixel basis and storing the resulting image in the memory; (k) creating a window of a predetermined size for sampling the dark-current corrected image; (l) positioning the window at a random location within the dark-current corrected image and sampling the dark-current corrected image; (m) calculating a mean grey level within the window, and calculating the standard deviation of the grey levels within the window; (n) calculating a variability factor as the ratio of the standard deviation to the mean grey level, and storing the ratio in a table in the memory; (o) repeating steps (k)–(n) a predetermined number of times and calculating a mean variability factor as the average of the variability factors of step (n) and storing the mean variability factor in the memory.

The method of the present invention is believed to be advantageous over the prior art in several ways. The illumination level is set for each sample so that the image will have a predetermined average grey level value at the midpoint (127.5) of the dynamic range of the digitization. As a result, a fixed digitizer contract enhancement window may be used for all samples. Also, the output of the light source need only be stable over the period of time during which the image is being acquired, typically only a few seconds. The uniformity measurement is independent of overall lightness differences between samples. The enhanced contrast images are corrected for camera dark current. This substantially removes contributions of the camera dark current from the measured grey level variation across the image. Since the dark current image may be captured and stored as often as desired, the uniformity measurement is effectively insensitive to CCD photodetector dark current spatial distribution variations over time, which may be related to temperature changes or aging effects in the camera CCD or electronics.

BRIEF DESCRIPTION OF THE FIGURES

FIG. 5 is a perspective view of the sample holding device.

DETAILED DESCRIPTION OF THE INVENTION

Apparatus

Figure 1:
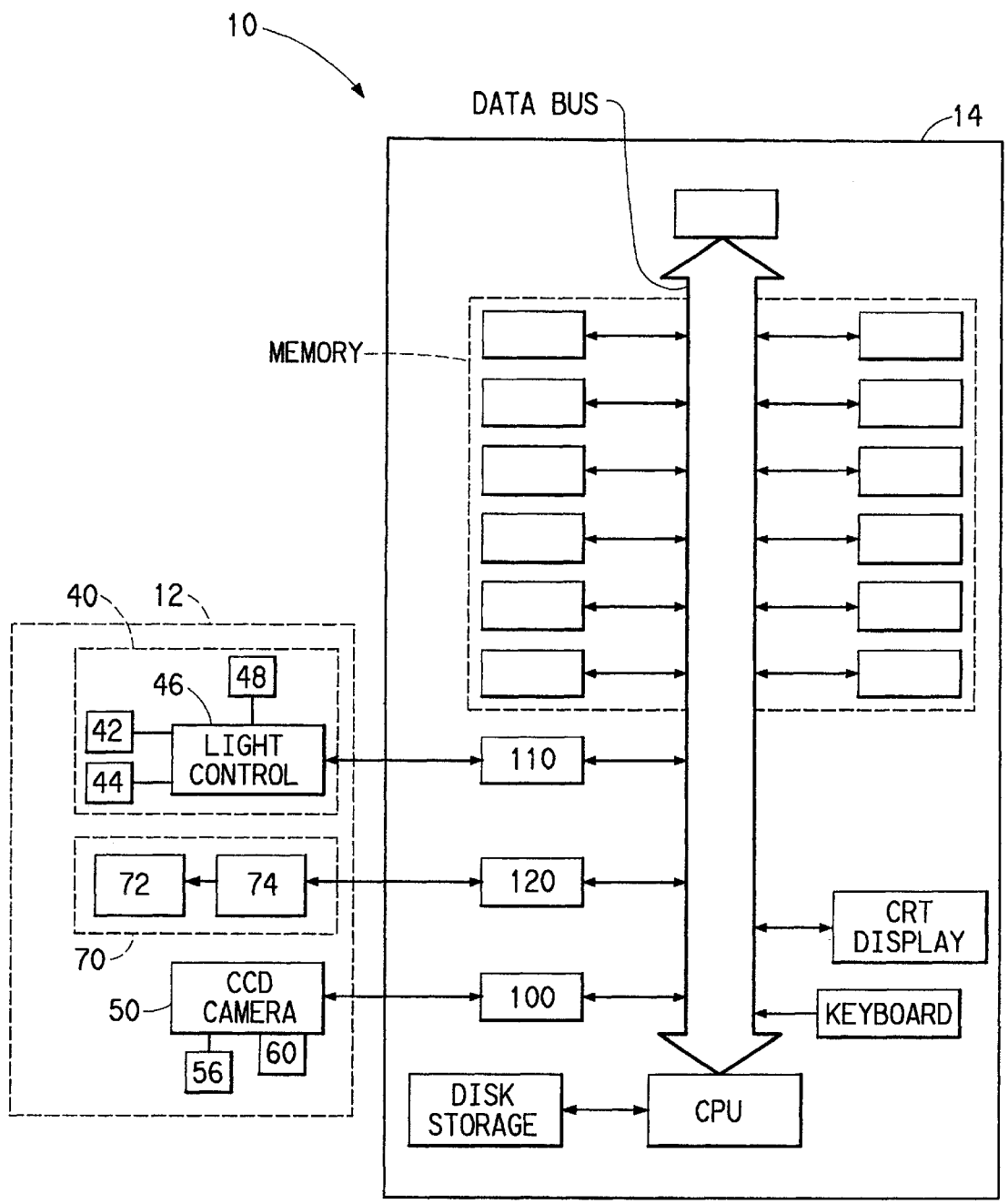
FIG. 1 is a stylized diagrammatic view of the elements of the invention.
Figure 2:
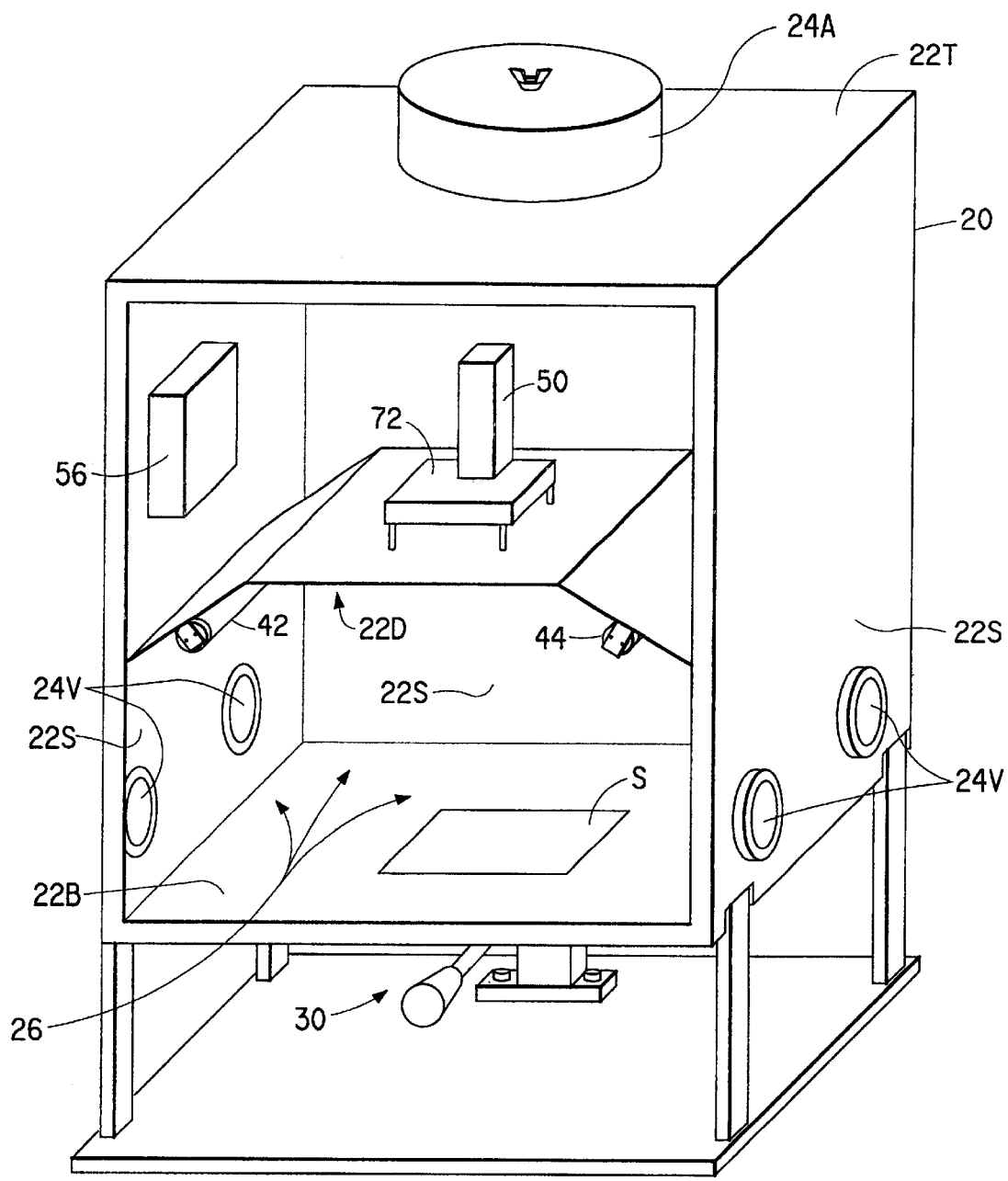
FIG. 2 is a stylized pictorial view showing the sample illumination and imaging assembly with the upper portion of the housing removed.
Figure 3:
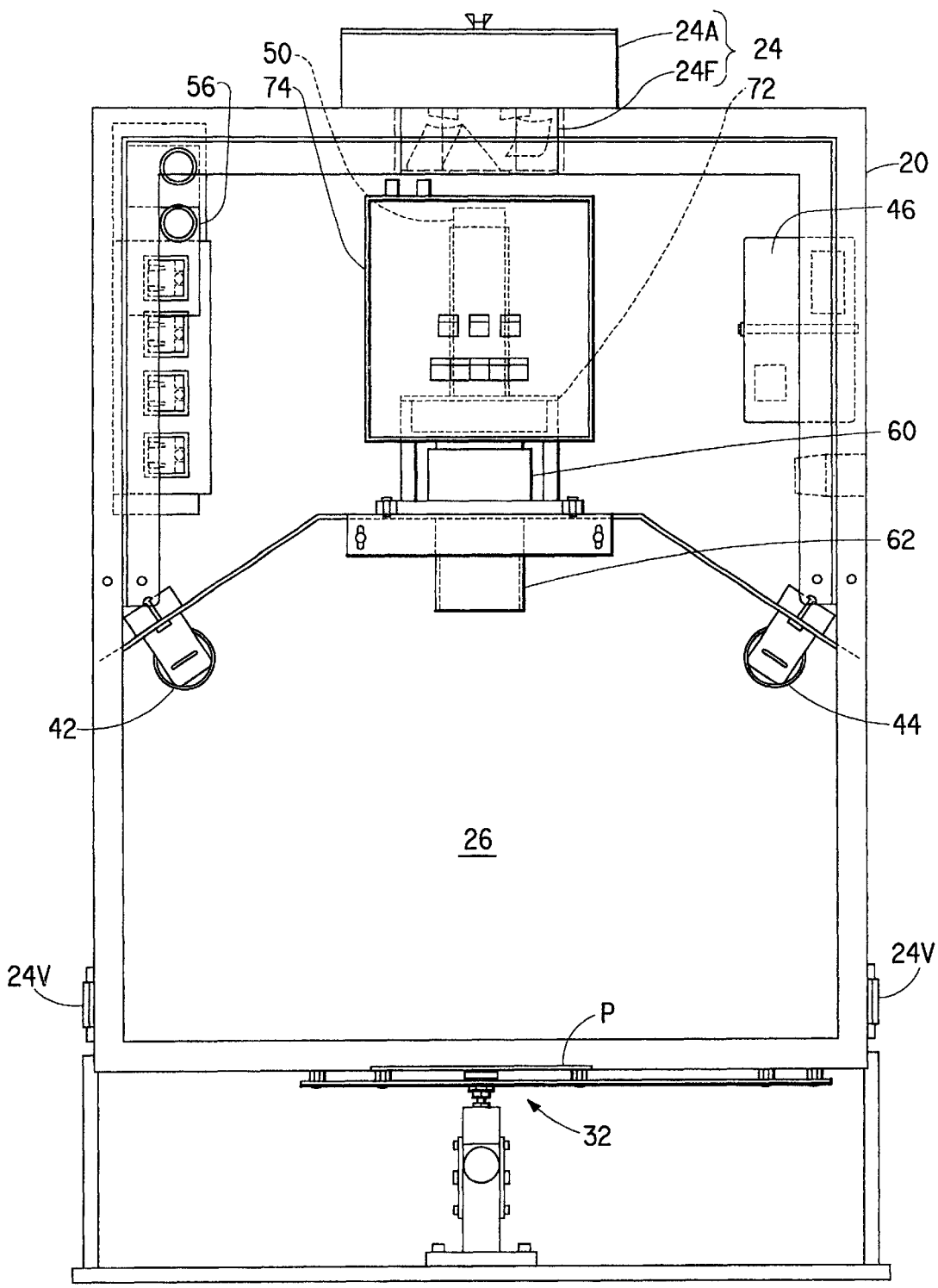
FIG. 3 is an elevational view, partly in section, showing the sample illumination and imaging assembly.
Figure 4:
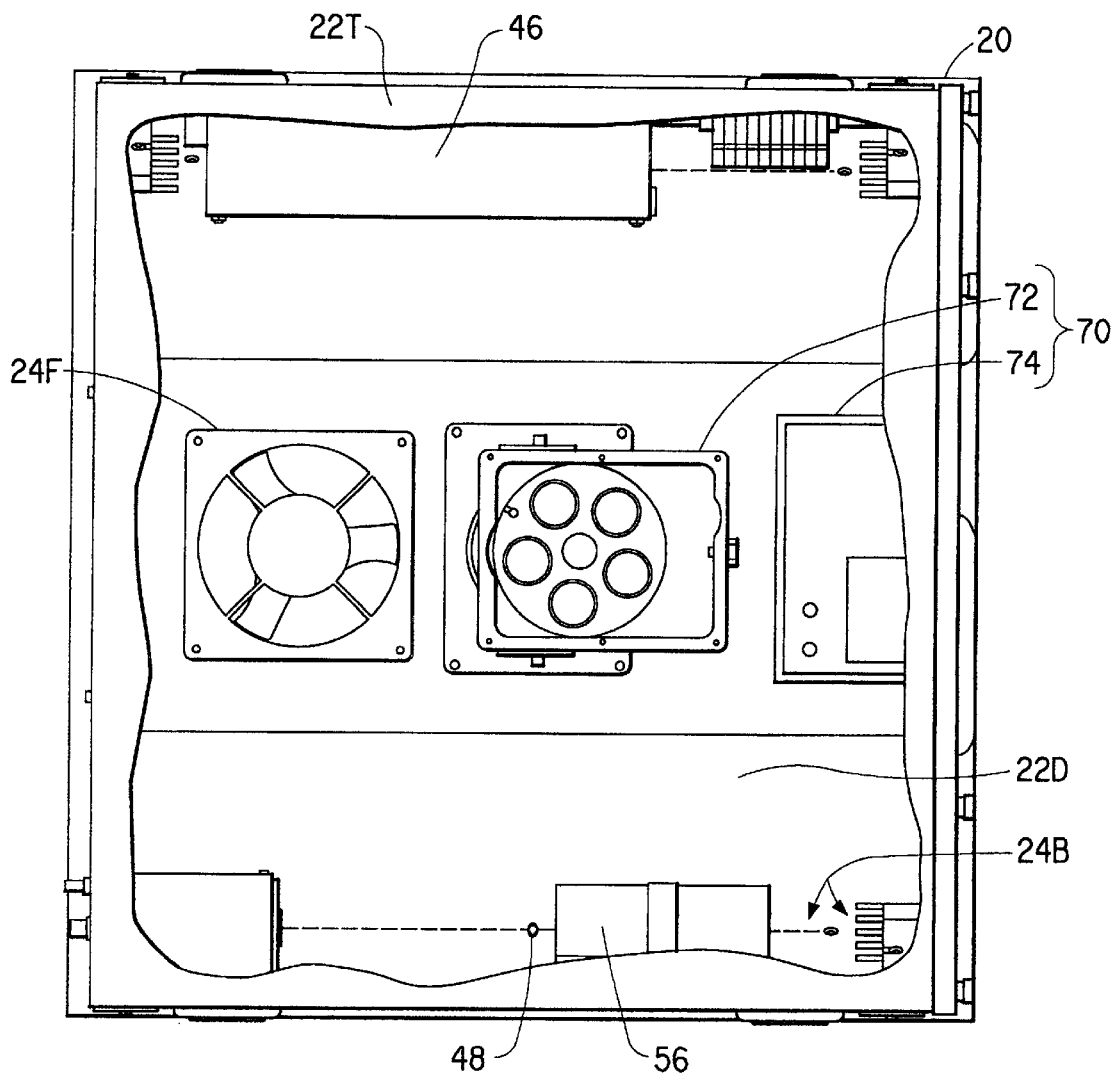
FIG. 4 is a plan view, partly in section, showing the sample illumination and imaging assembly.

The apparatus 10 of the present invention, as seen in FIG. 1, comprises a planar object imaging assembly 12, also referred to as the sample imaging assembly, and an associated computerized image processor 14. The planar object imaging assembly 12, best seen in FIGS. 2, 3 and 4, comprises a light-tight housing 20 in which are mounted a sample holding fixture 30, a fluorescent illumination assembly 40, a CCD camera 50, a photographic lens 60 and an optical filter assembly 70.

The housing 20 comprises a generally rectangular enclosure having a bottom wall 22B, side walls 22S, a top wall 22T and an interior dividing wall 22D. The sample holding fixture 30 comprises a generally planar clamping device 32 which holds a sample S flat in a holding frame 34 in the bottom wall 22B of the housing 20. The clamping device 32 is urged against the frame 34 by a spring 36. The frame 34 defines a sample plane P.

The fluorescent illumination assembly 40 which illuminates the planar sample S comprises two horizontally mounted 18-inch long F15/12 cool white fluorescent tubes, or lamps, 42, 44 which are mounted on the interior dividing wall 22D approximately 33 centimeters (13 inches) above the plane P of the sample S and are symmetrically disposed above the center C of the sample S approximately 40 centimeters (16 inches) apart. The lamps 42, 44 are powered by Mercron FX 0648-2 Model 600 controller 46 having a model CL9 photodetector accessory 48 which monitors the light output from the lamps and provides a feedback signal to the controller 46 to produce a precise output light level. The walls 22B, 22S, and 22D define a sample illumination chamber 26. The interior surfaces of the walls of the sample illumination 26 are covered with a high reflectivity, diffusely reflecting material, such as a flat white paint to provide a uniform illumination level to the surface of the sample S.

A ventilator assembly 24 comprising a fan 24F and an air filter assembly 24A is mounted on the top wall 22T to remove heat generated by the lamps of the fluorescent illumination assembly 40 and the power supplies and to stabilize the temperature of components within the housing. Associated air baffles 24B distribute air flow around the lamps 42, 44 to provide a more uniform temperature profile along the length of the lamps, which results in a more uniform light output. Air exits illumination chamber 26 through four one-way air valves 24V. This airflow also results in a longer useful life of the lamps.

The camera 50, the photographic lens 60, and the filter assembly 70 are fixedly mounted so that the photographic lens 60 projects an image of the sample plane P onto the photodetector 52 of the CCD camera 50. The lens 60 is mounted a fixed distance above the sample plane P, in accordance with the focal length of the lens. A suitable lens is a Nikon 28 mm focal length, f/2.8 lens which is mounted about 36 centimeters (14.25 inches) above the sample plane P. A lens hood 62 is employed to reduce stray light collected by the lens 60, which improves the fidelity of the image with respect to the actual light level across the sample.

The optical filter assembly 70 comprises a multiple position turret filter assembly 72, such as an Oriel model 77379 five position turret, which is located between the lens 60 and the CCD camera 50. The turret filter assembly 72 has five filter holders which respectively contain: 1) no filter; 2) a neutral density filter having a density of 0.1; 3) a neutral density filter having a density of 0.3; 4) a neutral density filter having a density of 0.5; 5) a black opaque filter. An associated turret control interface module 74, typically a Keitheley Microbyte model PIO-24 Digital I/O Board, is installed in the computerized image processor 14 so that the appropriate filter may be selected under software control. The purchased turret filter assembly 72 has been modified by machining to reduce the thickness dimension of the filter assembly 72 to enable mounting the assembly 72 between the lens 60 and the camera 50 to establish the proper lens-to-photodetector distance.

The camera 50, such as a Sony model XC77 video camera, powered by camera power supply 56, which comprises a CCD photodetector array and associated control and interface electronics, is mounted vertically with its CCD target about 46 centimeters (18.125 inches) above the sample plane P. The photographic lens 60 is typically set with its aperture at f/8. A field of view of about 11 centimeters by 8 centimeters (4.5 inch×3.5 inch) on the sample S is typically imaged.

Video images generated by the camera 50 are transmitted by a cable to the computerized image processor 14. The image processor 14 may comprise an IBM PC compatible computer having the customary Random Access Memory (RAM) 14R and magnetic storage devices 14M, containing a Matrox Pulsar video board 100, a Keitheley Microbyte model DAC-02 Digital to Analog (D/A) Board 110, and the Keitheley Microbyte model PIO-24 Digital I/O Board 120 therein. The computer may typically be controlled using the Windows-NT operating system, and the video board 100 may be controlled by associated software such as the Matrox Imaging Library Version 4.0. The Analog (D/A) Board 110 and the Digital I/O Board 120 may be controlled by associated software such as the Blue Water Systems WinRT device driver.

Video images, typically measuring 640 pixels wide by 480 pixels high, are digitized by an eight-bit (256 grey levels) analog to digital (A/D) converter in the video board 100 and are stored in a suitable memory device. A black reference level B and a white reference level W, which are software selectable, are used to control the upper and lower A/D voltages within the video board 100. These voltages determine the range of input voltages from the camera 50 which get mapped to the 256 grey levels (range of 0 to 255) of the A/D converter and hence determine the grey level contrast in the digitized image.

Image Contrast Enhancement

Figure 8:
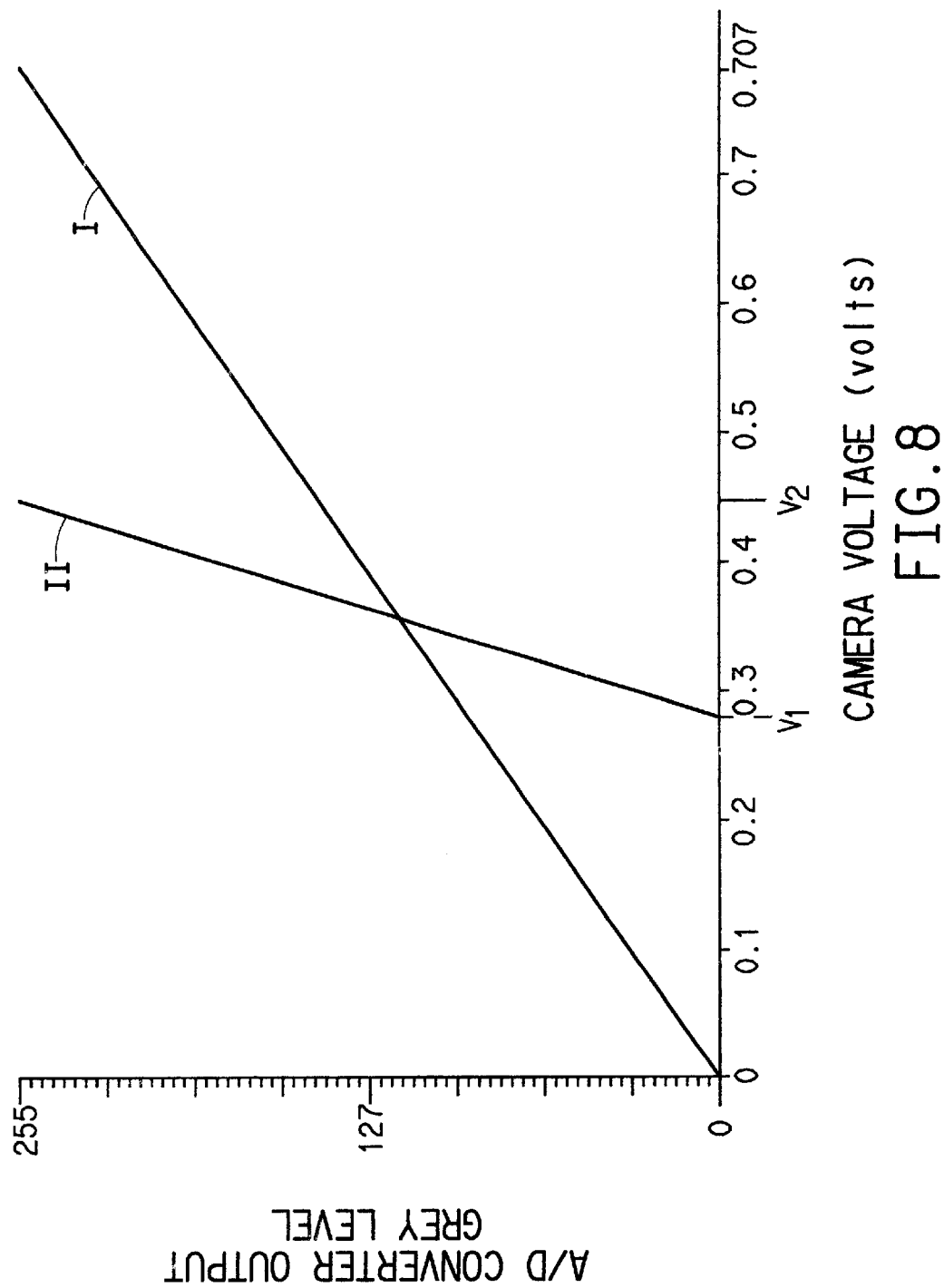
FIG. 8 is a plot showing the relation of the camera voltage and analog to digital converter grey levels.

The MdigReference function (part of the Matrox Library) allows setting of the reference levels used to digitize the video signal. In particular, the black reference M_BLACK_REF (referred to as B here) and the white reference M_WHITE_REF (referred to as W here) are used to select the lower and upper limit of video signal digitization. Each parameter varies between 0 and 255. The relationship between these parameters and camera voltage level are shown in FIG. 8. Varying the parameter B between 0 and 255 selects a particular camera voltage level $V_1$. Similarly, varying the parameter W between 0 and 255 selected a camera voltage level $V_2$.

The usual digitization relationship is given by line 1 in FIG. 8. Camera voltage levels between 0 (pedestal level) and 0.714 are digitized to grey levels between 0 and 255. This corresponds to B=0 and W=255. For other values of B and W the digitization relationship is given by line 11 in FIG. 8. Camera voltage levels between $V_1$ and $V_2$ are digitized to grey levels between 0 and 255. This results in increased image enhancement The following function relation exists between tile software parameters and the corresponding camera voltage digitization limits:

$$V_1 = \frac{0.357 B}{255} \quad (1)$$

$$V_2 = \frac{0.357 W}{255} + 0.357 \quad (2)$$

Preferred values are B=190 and W=57 which correspond to $V_1$=0.266 volts and $V_2$=0.437 volts, or a camera voltage range of 0.171 volts. The default camera voltage range is 0.714 volts (for a 1-volt peak-to-peak video signal). Thus image contrast is enhanced by a factor of 4.18 (default camera voltage range 0.174 divided by camera voltage range of 0.171).

Dark Signal Correction

The measurement parameter used in the present invention is based on the ratio of the standard deviation of grey levels to the mean grey level. The spatial variation of camera dark signal across an image, although usually small, can contribute to the measured standard deviation of grey levels. Also, the measurement parameter will be substantially independent of light level only when the dark signal is accounted for and the true image signal is measured. This section will describe the method derived for correcting the contrast-enhanced image for dark signal. This method was developed since simply capping the camera lens results in an image of all zero grey levels as the dark signal voltages are all outside the range $V_1$ to $V_2$.

From FIG. 8 it may be seen that the following function relation exists between image grey level and camera voltage:

$$g_u = \frac{255}{0.714} V_c \quad (3)$$

$$g_e = \frac{255}{V_2 - V_1}(V_c - V_1) \quad (4)$$

where $g_u$ refers to grey levels in the unenhanced image (curve I of FIG. 8) and $g_e$ refers to grey levels in the enhanced image (curve II of FIG. 8). Combining Eqs. (3) and (4).

$$g_e = \frac{0.714}{V_2 - V_1} g_u - \frac{255}{V_2 - V_1} V_1 \quad (5)$$

Eq. (5) gives the relationship between grey levels in the enhanced and unenhanced image, where the enhancement is based on the selection of values for $V_1$ and $V_2$. Thus, if a particular camera voltage level results in an image pixel With grey level $g_u$ based on line 1 in FIG. 8, then that pixel will have a grey level $g_e$ based on line 11 in FIG. 8. In particular. Eq. (5) can be applied to the grey levels of the dark signal image.

Thus, the procedure for correcting for dark signal is as follows:

Set B=0 and W=255 and sample the dark signal by blocking the camera lens. Store the dark signal image (with suitable frame averaging to improve the measurement).

For each pixel in the dark signal image, use Eq. (5) to calculate the corresponding dark signal grey level in the enhanced image and store these values in a memory buffer of the same size and format as the image.

After each enhanced sample image is digitized, subtract the values in the memory buffer, point by point, from the pixel values in the enhanced sample image.

As an example, for $V_1$=0.263 volts $V_2$=0.433 volts and an unenhanced gray level pixel value $g_u$=1.5, an enhanced gray level pixel value $g_e$=332 results.

Due to variations in electrical components, the actual camera voltage level limits for digitization, $V_1$ and $V_2$, that correspond to a selection of B=190 and W=57 may be different, for any given Matrox Pulsar digitizer board, from the expected values calculated using equations (1) and (2). These camera voltage level limits are used in equation (5) to calculate the multiplicative and additive terms that relate the grey levels in the enhanced and unenhanced images. For the most accurate dark signal correction, the actual values of these multiplicative and additive terms should be determined by measurement. Several alternative procedures can be used.

One method for refining the dark signal correction is to use a video oscilloscope, such as the Sony Tektronix 380 NTSC Test Monitor, to measure the camera voltage corresponding to a particular location in the image. The light level is varied to provide a range of camera voltage levels. For each setting of the light level, the grey level (average of several neighboring pixels) in the same image location being monitored by the video oscilloscope is measured with black reference level. B, set to 190 and white reference level, W, set to 57. From a least squares fit of the camera voltage data as a function of the grey level to a straight line function, one can calculate the camera voltage, $V_1$, corresponding to a grey level of 0 and the camera voltage, $V_2$, corresponding to a grey level of 255. As an example for a particular Matrox Pulsar board, for B=190 and W=57, equations (1) and (2) lead to the following values: $V_1$=0.266 volts and $V_2$=0.437 volts. Using the measurement procedure just described, we find $V_1$=0.267 volts and $V_2$=0.447 volts. Using these values of $V_1$ and $V_2$ in equation (5), and applying the dark signal correction method, it is found that paperboard measurements (as described below) are substantially independent of the target image average grey level selected, that is, independent of light level. For example, for a particular paperboard, the measurements (as described below) varied only between 2.33 and 2.42 for target image average grey levels in the range 75 to 220. This substantial measurement independence from light level indicates that the dark signal correction method is working properly. Without the refinement in the values of $V_1$ and $V_2$, the measurement values differed by about one unit over a smaller range of light levels.

Other methods for refining the dark signal correction involve direct determination of the multiplicative and additive terms in equation (5) without knowledge of the $V_1$ and $V_2$ values. A large number of grey levels are measured using the same set of pixel locations in two different images, using the same light level setting in both cases. In the first, image, B=0 and W=255 are used. In the second, contrast enhanced, image. B=190 and W=57 are used. The light level should be set so that there are substantially no pixels at grey levels of 0 or 255 in either image. Since individual pixel grey levels are used, video frame averaging will lead to more accurate results. This procedure results in two sets of grey levels, $g_i$ (enhanced) and $g_i$ (unenhanced), where the grey levels for a particular value of i correspond to the same pixel location in the image. By doing a least squares fit to a straight line function of $g_i$ (enhanced) as a function of $g_i$ (unenhanced), one directly obtains from the least squares function the multiplicative and additive terms in equation (5). A sample that results in a wide range of grey levels in each image should be used to obtain a satisfactory least squares fit.

Another method for refining the dark signal correction that involves direct determination of the multiplicative and additive terms in equation (5) makes use of the linear nature of equation (5). That is, the relationship between the grey levels at a particular pixel location in the enhanced and unenhanced images also holds for the average grey level in a selected region of the enhanced image and the average grey level in the same region in the unenhanced image. In the image with B=0 and W=255, one can select two regions, say, region 1 and region 2, in the image and calculate, for a given light setting, the average value of grey level in each region: $G_1$ (unenhanced) and $G_2$ (unenhanced). Similarly, in the image with B=190 and W=57, one calculates the average grey level in the same two regions and for the same light level setting: $G_1$ (enhanced) and $G_2$ (enhanced). Video frame averaging should be used for each image to improve the accuracy of the method. Also, the larger the region, the more pixels are averaged, also leading to improved accuracy. The following relationships apply;

$$G_1(\text{enhanced}) = \alpha G_1(\text{unenhanced}) + \beta \quad (6)$$

$$G_2(\text{enhanced}) = \alpha G_2(\text{unenhanced}) + \beta \quad (7)$$

These two simultaneous equations can be solved for $\alpha$ and $\beta$ which are respectively the multiplicative and additive terms in equation (5). A sample that results in substantially different values of average grey level between region 1 and region 2 should be used. Alternatively, one can select more than two regions and do a least squares determination of $\alpha$ and $\beta$ as described above for individual pixel grey levels. Averaging over a substantial number of pixels in each region for the determination of $G_1$, should lead to improved accuracy over the above described least squares method based on individual pixel grey levels.

Control of Illumination Level

Figure 6A:
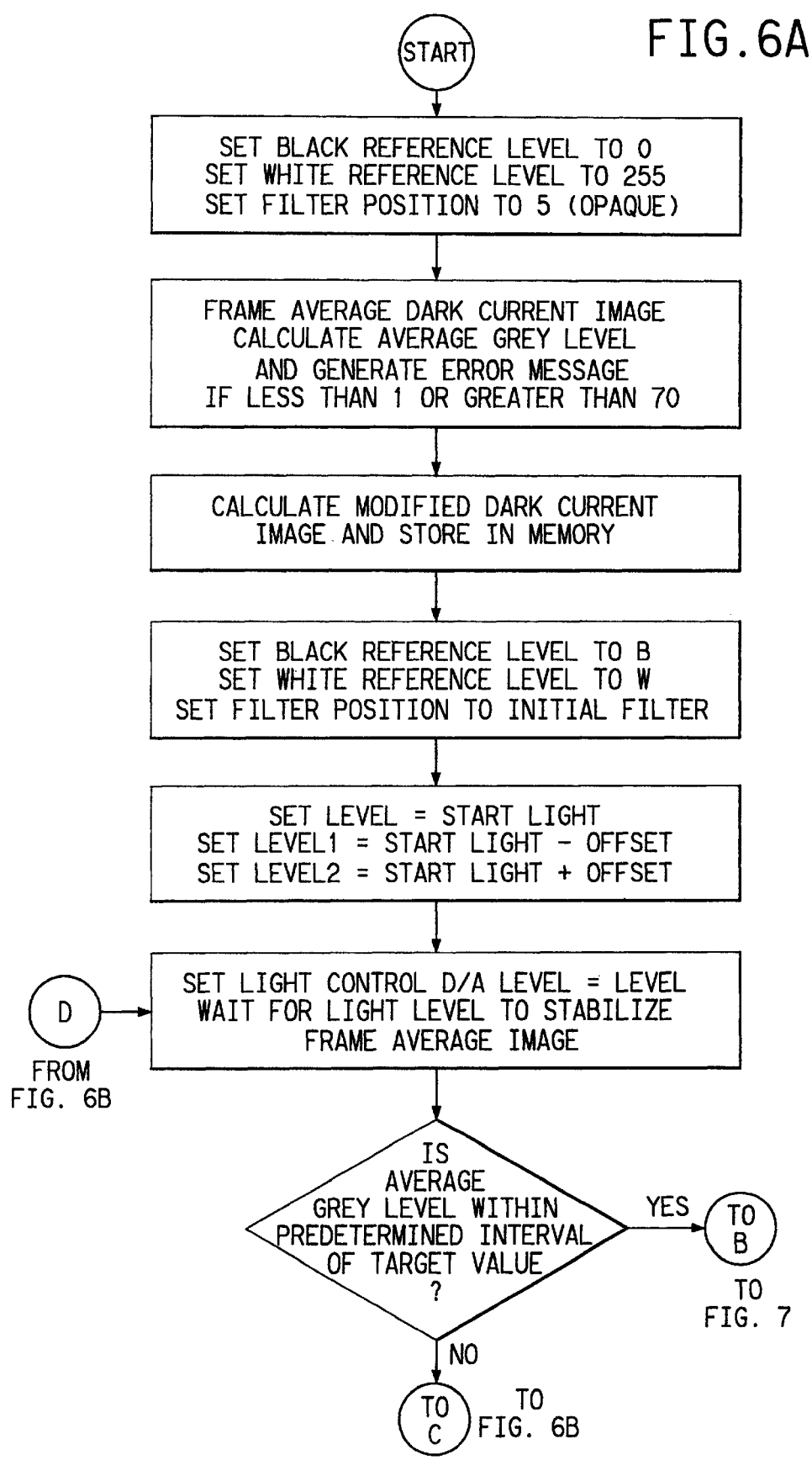
FIGS. 6A–6B are a block diagram illustrating a method of adjusting the illumination level of the sample.
Figure 6B:
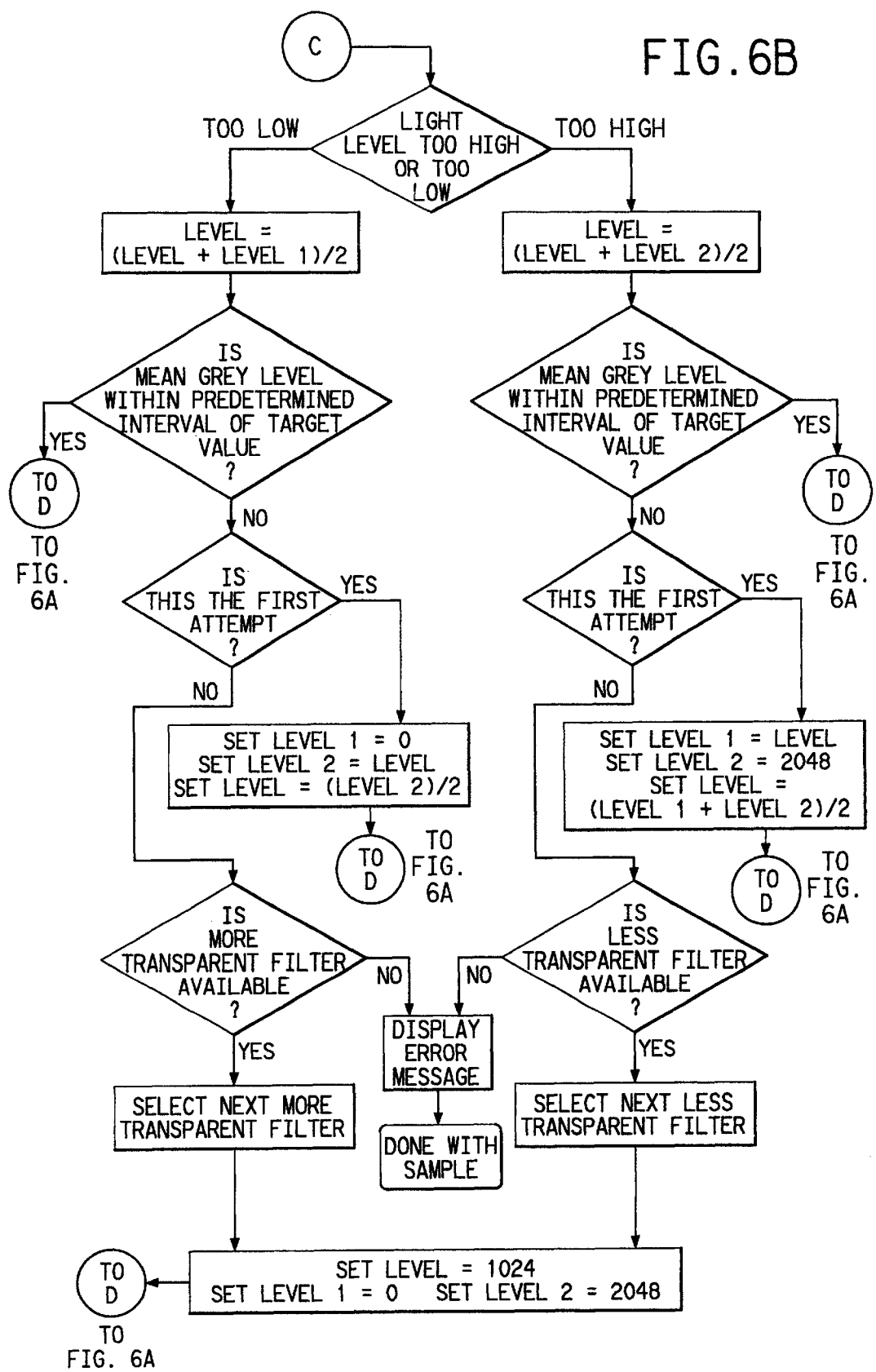
Figure 7:
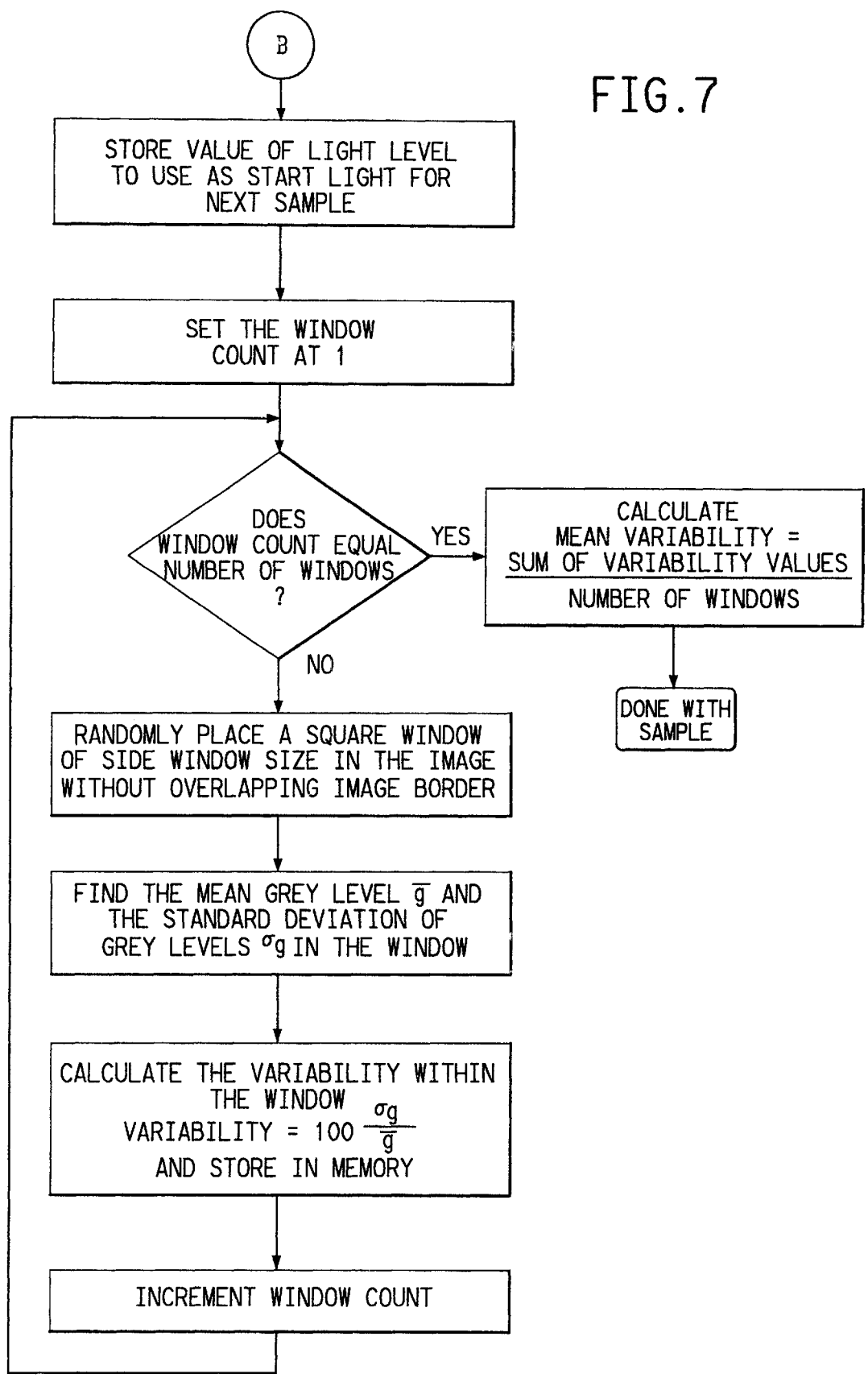
FIG. 7 is a block diagram illustrating a method of calculating the variability of the sample.

As may be seen in FIGS. 6A–6C, the computerized image processor 14 is programmed to precisely control the light level illuminating the sample S. This is accomplished by first setting the analog to digital converter to map the contrast enhanced camera voltage range to the full grey level output range. The surface of the object is illuminated with the light source, with the light source being set to an initial output level. A digitized frame-averaged image of the surface is created by first imaging the light reflected from the surface onto the photodetector array to create an electrical signal representative of the image. The electrical signal is digitized and frame averaged a predetermined number of times and the frame averaged representation of the image is stored in the image processor memory. The average grey level in the image is determined and the illumination level of the object is adjusted until the average grey level in the image is at a desired level, typically the midpoint of the dynamic range of the analog to digital converter. This is done by adjusting the output of tithe light source and repeating steps of acquiring an image, determining the average grey level and adjusting the illumination level until the average light level reflected by the surface of the object causes an average grey level in the image of to be within a predetermined range of the midpoint of the enhanced contrast dynamic range of the analog to digital converter. If adjusting the illumination level alone does not result in the desired average grey level, then a different optical density filter is selected in combination with adjusting the output of the light source until the average light level reflected by the surface of the object causes the CCD array to produce an output within a predetermined range of the midpoint of the enhanced contrast dynamic range of the analog to digital converter.

To accelerate the measurement method the initial illumination level is set by initially setting the light source output level to the level used for the previous sample and illumination adjusting step is first performed using a binary search method to set tile light source output level within a predetermined range of light levels. If the desired average grey level is not achieved, the illumination adjusting step is then performed using a binary search method to set the light source output level over the full range of light levels. If the desired average grey level is still not acheived a different optical density filter is selected and the illumination adjusting step is performed using a binary search method to set the light source output level over the full range of light levels. If no previous illumination level is known, the density of the optical density filter is initially selected at a midrange density value and is subsequently reselected if adjustment of the output of the light source cannot produce an output at the midpoint of the enhanced contrast dynamic range of the analog to digital converter.

Analysis Method

With the full 1.2 volt range of A/D voltages selected (Black Reference level=0, White Reference level=255, i.e., no enhancement of the image), the camera lens is capped, by selecting filter position 5 which contains the opaque filter so that no light reaches the CCD array. The image produced by the camera in the absence of light, known as the "dark response" or "dark current" image, is digitized a predetermined number of times (typically 128) and then frame averaged. That is, the corresponding picture elements, or pixels, in each of the images are added and then divided by the number of images digitized to produce an image which represents the average dark current response of the CCD array and its associated electronics. This so called "average dark current" image is stored in memory, such as RAM or magnetic storage media, for subsequent use.

The average dark current image can be used to correct each pixel in the paperboard image as follows. The average dark current image is first converted to a "modified dark current image" to correspond to the contrast range of the subsequent enhanced sample images in accordance with Equation (5). This modified dark current image is stored in memory and subsequently subtracted from each enhanced sample image.

The method of creating the frame-average modified dark current image comprises the steps of; (1) setting the analog to digital converter to map the full camera voltage range to the full grey level output range; (2) digitizing and frame averaging the electrical signal from the CCD photodetector array in the absence of light a predetermined number of times to create an averaged dark current image; (3) storing the frame-averaged dark current image in the memory; (4) applying the transformation factors to create a modified dark current image; (5) storing the modified dark current image in the memory.

For each sample, the light level is automatically set so the camera output voltage to the A/D converter is such that the average grey level in the image is in the range 127.5+/−10. The black reference level B and the white reference level W reference voltages are set using fixed values: Black=190, White=57. This causes a 0.17 volt wide A/D voltage window to be centered at the 0.35 volt center A/D voltage level and results in a grey level contrast enhancement of a factor of 4.16. The light level produced by the fluorescent lamps is automatically controlled by the digital to analog (D/A) board 110 in the computer to provide a reference voltage input to the Mercron controller 46.

Each sample image is frame averaged a predetermined number of times (typically 64) and the modified dark current image is then subtracted from it on a pixel by pixel basis to produce a "dark current corrected image".

Image Analysis Algorithm

The image is statistically sampled using a window of a predetermined size randomly positioned within the image. The window size is selected to correspond to the spatial scale of the image features of interest that are observable by the human evaluator. Since the analysis window size and the corner coordinates of the image are known, random numbers specifying the window are generated for random placement of the analysis window in the image without overlapping the image border. For paperboard the window is typically a square 31 picture elements on a side and the number of randomly positioned windows is typically about 500. It should be noted that if the window size is too large, then shading due to illumination variations within each window will affect the measurement. On the other hand, if the window size is too small, then the features of interest, such as mottle, cannot be detected adequately. Increasing the number of randomly positioned windows will not significantly improve the correlation to human observations but take longer to run. Using too few randomly positioned windows will produce "noisier" results and hence poorer correlation to human observations.

The analysis procedure comprises:

a) Generate a square window of side=31 picture elements and randomly place it in the image.

b) Find the mean grey level, $g_{av}$, and the standard deviation of grey levels, $\sigma_g$, within the box.

c) Calculate the "variability", $V_i$, within the window:

$$V_i = 100\sigma_g/g_{av}$$

and store this vale in memory:

d) Repeat steps a) to c) 500 times;

e) Calculate the average variability, called the mean variability factor $V_{av}$, over all windows:

$$V_{av} = \frac{\sum_{1}^{500} V_i}{500}$$

and store this value in memory.

Region of Interest

The system of the present invention has the capability to restrict measurement on a sample to a region of interest (ROI) in the field of view. The ROI is specified by the user interactively through placement of a cursor box, which is displayed superimposed on an image of the sample, that is moved and sized by pressing appropriate keys on the terminal input device to the image processor 14.

In the standard analysis method, all of the image is measured. Since the analysis window size and the corner coordinates of the full image are known, random numbers specifying the window center are generated for random placement of the window in the image without overlapping the border. The corner coordinates of the region of interest are similarly employed so that the analysis window does not overlap the border of the region of interest.

For meaningful results, there should be a lower limit to the size of the region of interest, which is typically 100×100 pixels. Otherwise, the necessarily smaller analysis window might be too small to effectively measure the characteristics of interest of the surface.

EXAMPLE

The method of the invention was used to characterize a set of 14 paperboard samples. Twelve people took part in a paired-comparison rating test to visually rank the uniformity of the 14 samples. Each participant was instructed to rank the 14 samples according to observed uniformity. For applications such as paperboard the mean variability factor is scaled used in a fixed scaling factor for all samples so that the typical sample has a value in the range of 1 to 10.

Each paperboard sample, which was identified with an arbitrary number from 1 to 14, was given a rating from 1 (most uniform) to 14 (least uniform) by each person. This ranking data was collected. A so-called "trimmed average" rating and standard deviation of ratings was computed for each sample. The "trimmed average" rating was obtained by removing from the ranking data for each sample the one rating which was most different from all others.

Figure 9:
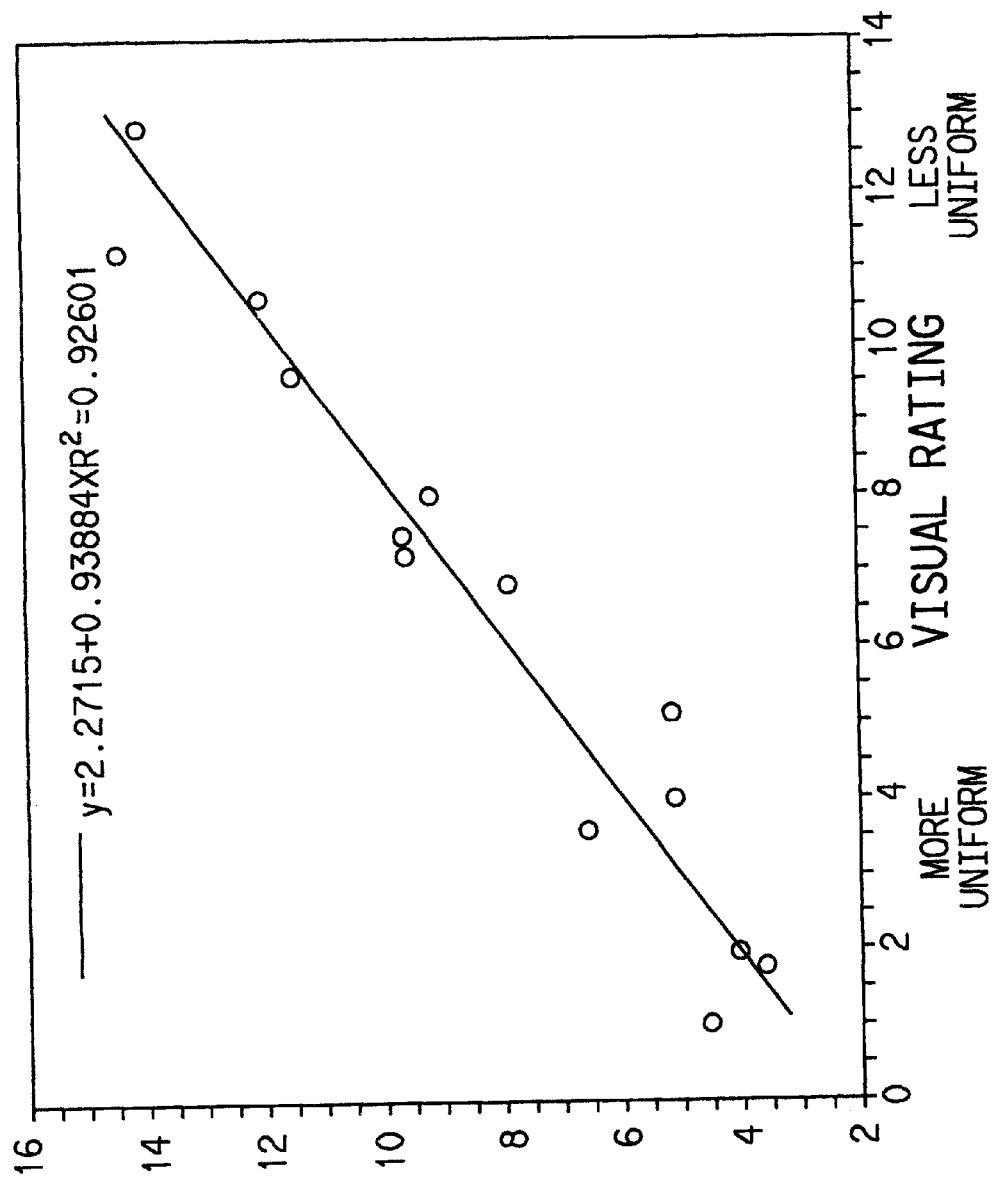
FIG. 9 is a plot showing the correlation of the output of the inventive method plotted against the trimmed average ratings produced by a panel of human observers.

The same 14 samples were analyzed automatically using the apparatus and the method of the present invention as described above. The results of the visual ratings and the results of the method of the present invention are presented in Table 1. The rating obtained using the inventive method was plotted against the trimmed average values of visual ratings, as shown in FIG. 9. As may be appreciated from FIG. 9 the correlation between the inventive method and the visual uniformity ratings is quite high, specifically about 0.92.

The repeatability of the inventive method is quite high. For example, ten images of a typical sample were obtained (without moving the sample) and analyzed. The average of the mean variability factor was 4.870 and the standard deviation was 0.034. This is equivalent to a percent coefficient of variation (% CV) of 0.71. Thus, it may be concluded that the major limitation in correlating the inventive results to the visual ratings is the rather high standard deviations of the visual ratings. This may be best appreciated by review of the results summarized in Table 1.

TABLE I

| Visual Rating | Standard Deviation | Inventive Method |
| --- | --- | --- |
| 8.00 | 3.08 | 9.08 |
| 4.00 | 1.89 | 5.19 |
| 10.60 | 1.40 | 11.99 |
| 11.10 | 1.54 | 14.48 |
| 12.80 | 0.40 | 13.92 |
| 7.40 | 1.50 | 9.56 |
| 9.50 | 1.40 | 11.31 |
| 5.30 | 2.04 | 5.14 |
| 7.10 | 2.62 | 9.50 |
| 1.90 | 1.62 | 4.04 |
| 3.50 | 2.23 | 6.53 |
| 6.70 | 1.57 | 7.88 |
| 1.70 | 1.21 | 3.67 |
| 1.00 | 1.14 | 4.57 |

What is claimed is:

1. A method for measuring variations of the optical reflectance of a substantially planar object having a reflective surface that includes the steps of illuminating the surface of said object with a light source, imaging the light reflected from the surface onto a photodetector array to create an electrical signal representative of the image, digitizing the electrical signal using an analog to digital converter, storing the digitized representation of the image as an array of picture elements in a memory, and analyzing the digitized representation, the improvement comprising:

(a) utilizing an analog to digital converter whose dynamic range may be set to a first, full, range and set to a second, contrast enhanced, range;

(b) establishing transformation factors based upon the lower and upper limits of the first range and the second range of the analog to digital converter;

(c) creating a frame-averaged modified dark current image representing the response of the photodetector array in the absence of light;

(d) setting the analog to digital converter to map the contrast enhanced camera voltage range to the full grey level output range;

(e) illuminating the surface of the object with the light source, the output of the light source being set to an initial output level;

(f) creating a frame-averaged image of the surface of the object;

(g) determining the average grey level in the image;

(h) adjusting the illumination level of the object by adjusting the output of the light source and repeating steps (f) and (g) until the average light level reflected by the surface of the object causes an average grey level in the image of step (g) to be within a predetermined range of the midpoint of the enhanced contrast dynamic range of the analog to digital converter;

(i) creating a frame-averaged image of the surface of the object;

(j) creating a dark-current corrected image by subtracting the frame-averaged modified dark current image of step (c) from the frame-averaged image of the surface of step (i) on a pixel by pixel basis and storing the resulting image in the memory;

(k) creating a window of a predetermined size for sampling the dark-current corrected image;

(l) positioning the window at a random location within the dark-current corrected image and sampling the dark-current corrected image;

(m) calculating a mean grey level within the windows and calculating the standard deviation of the grey levels within the window;

(n) calculating a variability factor as the ratio of the standard deviation lo the mean grey level, and storing the ratio in a table in the memory;

(o) repeating steps (k)–(n) a predetermined number of times and calculating a mean variability factor as the average of the variability factors of step (n) and storing the mean variability factor in the memory.

2. The method of claim 1, wherein the step (c) of creating the frame-averaged modified dark current image comprises the steps of:

(1) setting the analog to digital converter to map the full camera voltage range to the full grey level output range, (2) digitizing the frame averaging tile electrical signal from the CCD photodetector array in the absence of light a predetermined number of times to create an averaged dark current image, (3) storing the frame-averaged dark current image in the memory, (4) applying the transformation factors to create a modified dark current image, (5) storing the modified dark current image in the memory.

3. The method of claim 1, wherein the steps (1) and (i) of creating the frame-averaged image of the surface of the object each comprise the steps of:

(1) imaging the light reflected from the surface onto the photodetector array to create an electrical signal representative of the image;

(2) digitizing and frame averaging the electrical signal a predetermined number of times;

(3) storing the frame averaged representation of the image in the memory.

4. The method of claim 1, further comprising a selectable optical density filter positioned between the lens and the CCD array, and further comprising, in the illumination level adjusting step (h), selecting the density of the optical density filter in combination with adjusting the output of the light source so that the average light level reflected by the surface of the object causes the CCD array to produce an output within a predetermined range of the midpoint of the enhanced contrast dynamic range of the analog to digital converter.

5. The method of claim 4, wherein the density of the optical density filter is initially selected at a midrange density value and is subsequently reselected if adjustment of the output of the light source cannot produce an output at the midpoint of the enhanced contrast dynamic range of the analog to digital converter.

6. The method of claim 1, wherein a known set of calibration standards are imaged and further comprising the step of:

(p) normalizing the mean variability factor by:

(1) performing a least squares fit to a quadratic equation of expected mean variability factors as a function of measured mean variability factors to determine a set of quadratic coefficients;

(2) using the measured value of the mean variability factor in the quadratic equation to produce the normalized mean variability factor.

7. The method of claim 1, wherein the illumination adjusting step (h) is performed using a binary search method within a predetermined range of light levels.

8. The method of claim 1, wherein the illumination adjusting step (h) is performed using a binary search method within the full range of light levels.

9. The method of claim 4, wherein the illumination adjusting step (h) is performed using a binary search method within tile full range of optical density filters and within the full range of light levels.

10. The method of claim 1, wherein a region of interest (ROI) is the filed of view is selected before performing step (l) through (o).

* * * * *